United States Patent [19]

Doucette

[11] Patent Number: 5,146,685
[45] Date of Patent: * Sep. 15, 1992

[54] MULTI-DIMENSIONAL SURGICAL BLADE HOLDER AND BLADE COMBINATION

[75] Inventor: Thomas H. Doucette, West Milford, N.J.

[73] Assignee: Becton, Dickinson and Company, Franklin Lakes, N.J.

[*] Notice: The portion of the term of this patent subsequent to Oct. 29, 2008 has been disclaimed.

[21] Appl. No.: 645,387

[22] Filed: Jan. 24, 1991

Related U.S. Application Data

[63] Continuation-in-part of Ser. No. 612,356, Nov. 13, 1990, Pat. No. 5,060,387.

[51] Int. Cl.$^5$ .............................................. B26B 1/00
[52] U.S. Cl. ................................... 30/330; 30/337; 30/339; 606/167
[58] Field of Search ................ 30/329, 330, 331, 337, 30/339; 606/167

[56] References Cited

U.S. PATENT DOCUMENTS

| | | | |
|---|---|---|---|
| 1,554,083 | 9/1925 | Goldman | 30/339 |
| 1,823,001 | 9/1931 | Rassier | 30/331 |
| 2,464,206 | 3/1949 | Becker | 30/304 |
| 2,708,313 | 5/1955 | Steele | 30/339 |
| 3,262,205 | 7/1966 | Arden | 30/338 |
| 4,617,738 | 10/1986 | Kopacz | 30/339 |
| 4,746,016 | 5/1988 | Pollak et al. | 30/339 |

Primary Examiner—Frank T. Yost
Assistant Examiner—Hwei-Siu Payer
Attorney, Agent, or Firm—Robert P. Grindle; Nanette S. Thomas

[57] ABSTRACT

A combination of surgical blade holder and cooperating blade is provided, which allows simple insertion of a blade having a specific configuration of opening in the tang for receiving a specific boss configuration on the handle, and closure to a locked position of the blade, upon insertion. The two parts of the handle pivot relative to one another in the same longitudinal plane around a pivot positioned adjacent the blade portion. This allows a relatively long handle portion for gripping the device for ejecting the blade, using the thumb or finger of the same hand for opening the holder. The gripping portion of the handle has adjacent to the blade portion thereof a boss which conforms to the opening in the blade tang. The boss includes a cleat with an overhang which serves to receive the opposed mating surface on the opposite half of the handle. The cooperating surfaces on the blade and handle provide three dimensional gripping of the blade closure which causes the movable portion of the handle to cover the boss and the blade tang. The mating surfaces on the handle include opposed surfaces for gripping the blade rib. When opening, the user pushes the movable portion of the handle open while holding the blade and boss of the fixed handle portion facing downward so that the blade falls out of the device, without any touching or movement of any kind, into a collector.

12 Claims, 6 Drawing Sheets

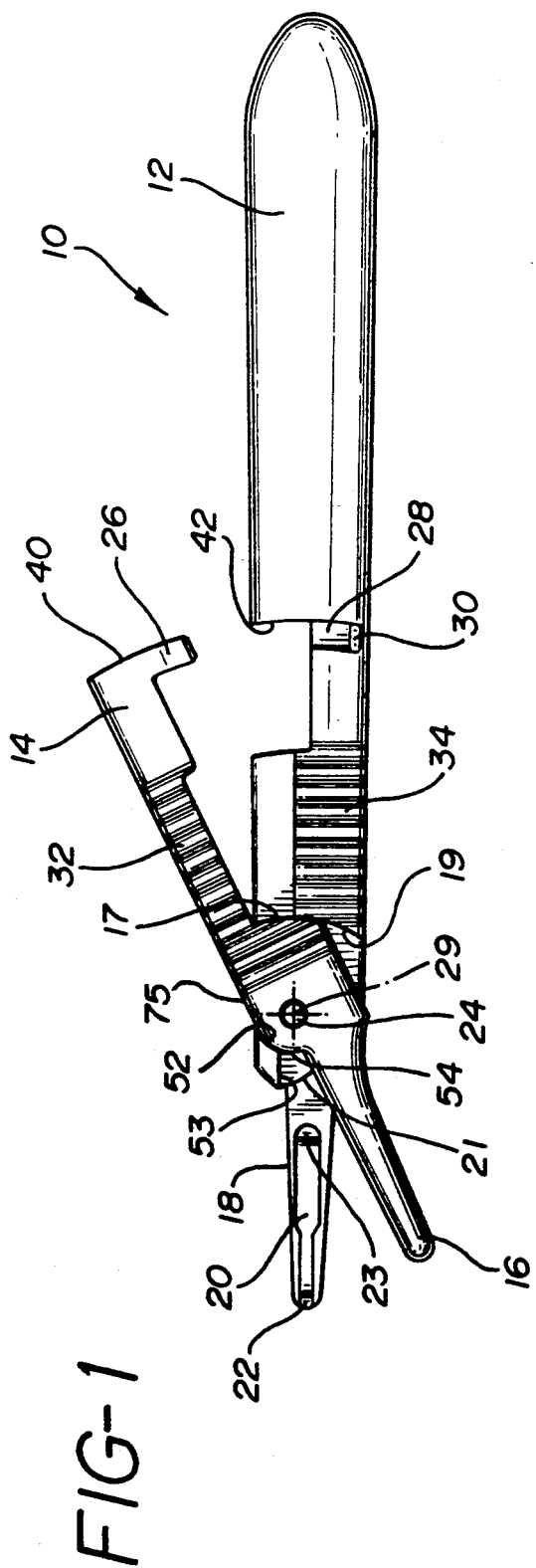
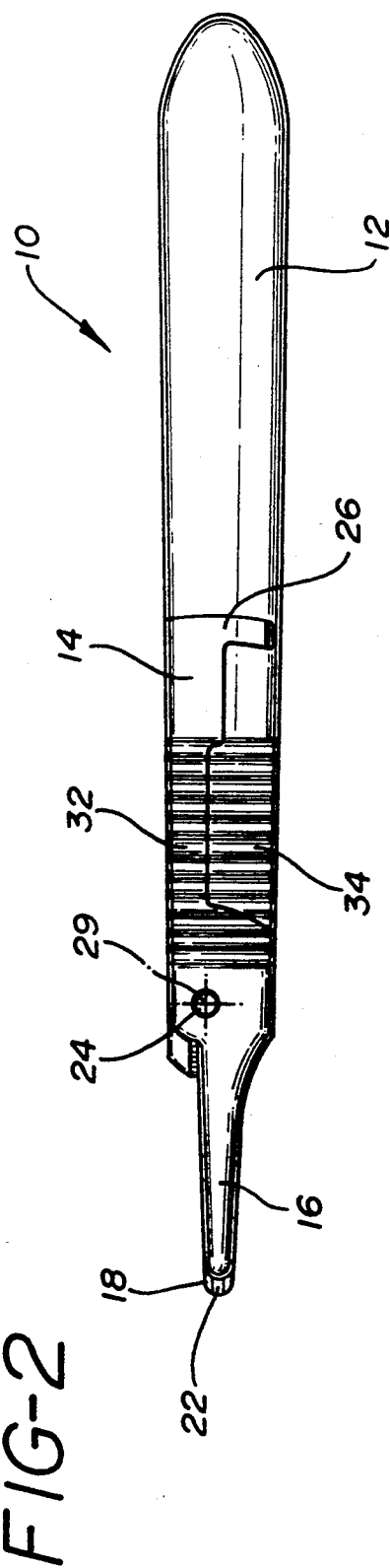

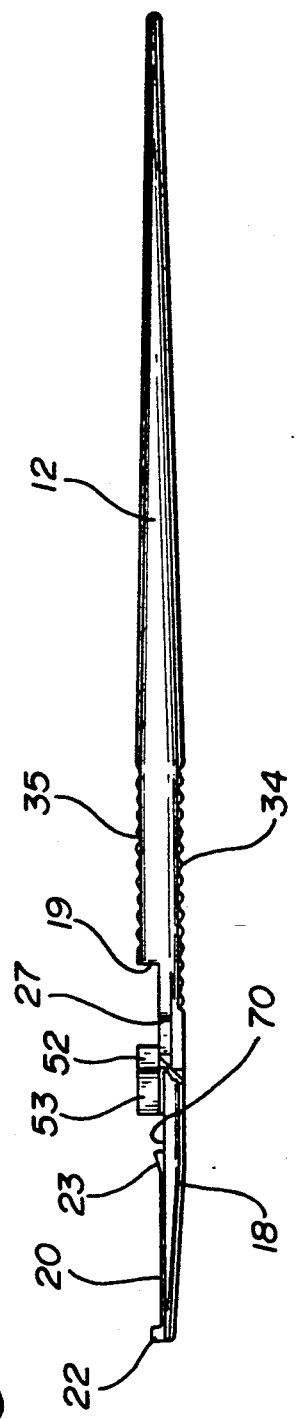
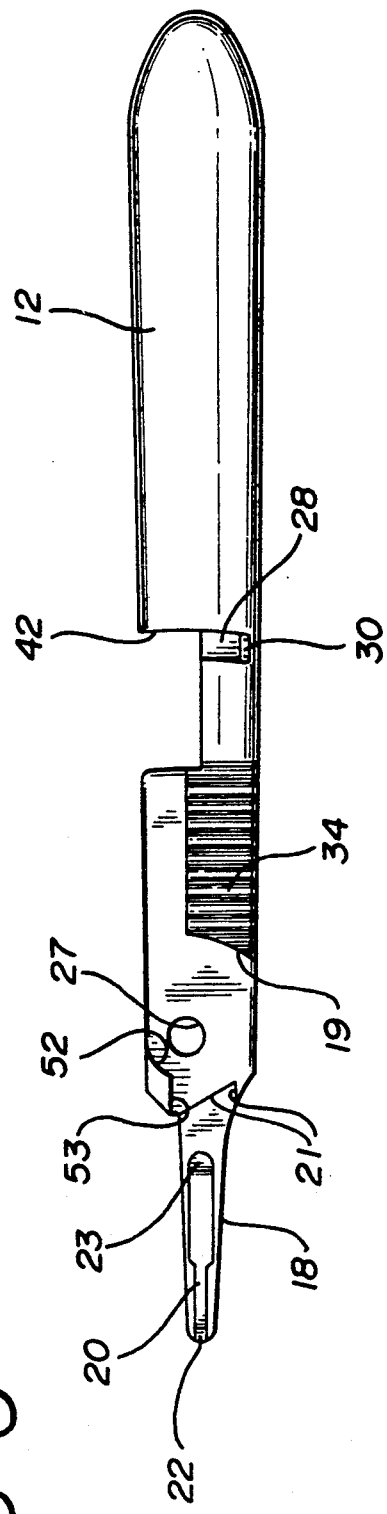

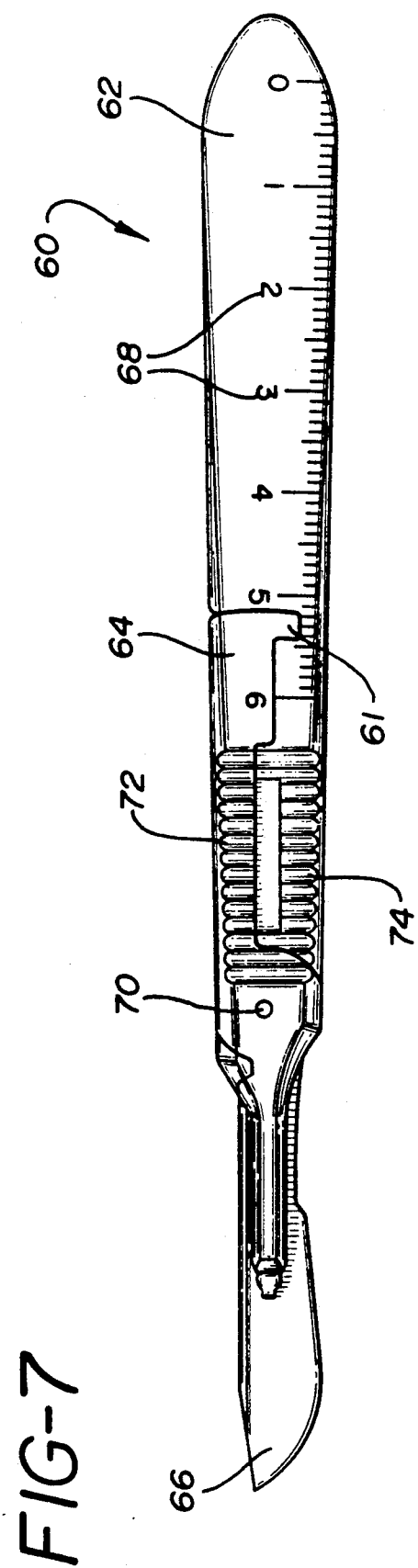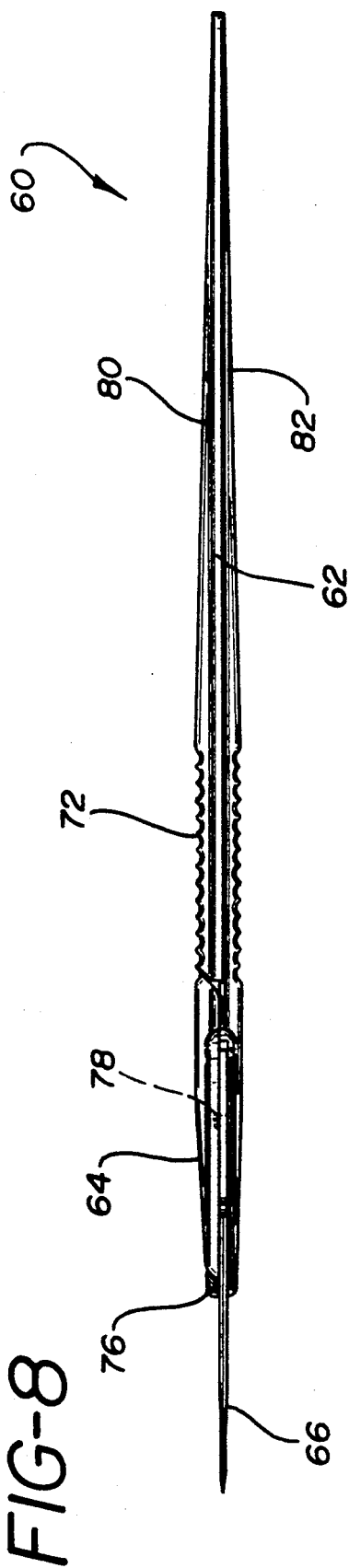

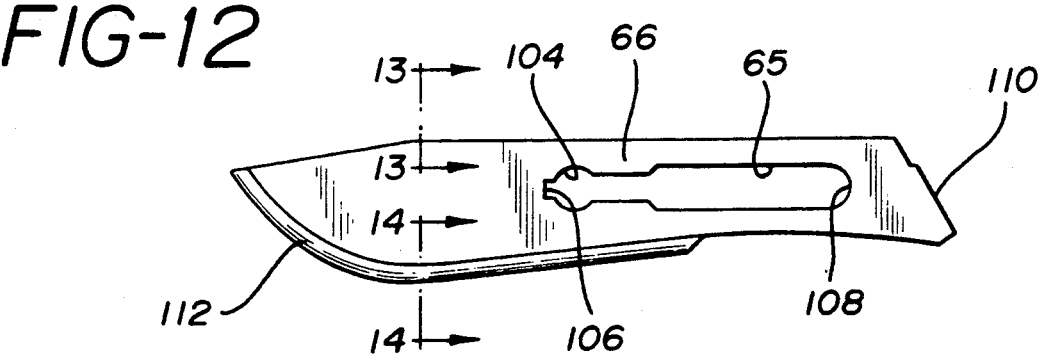
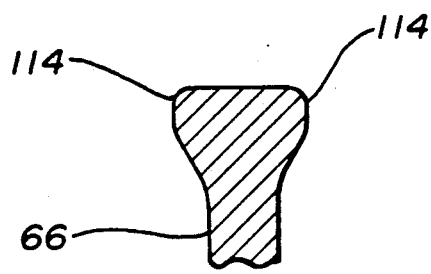
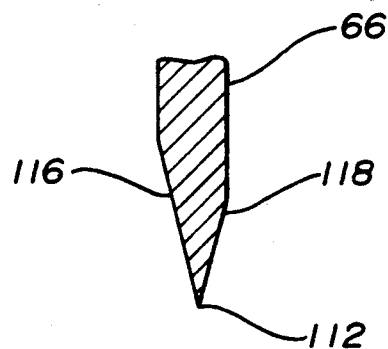
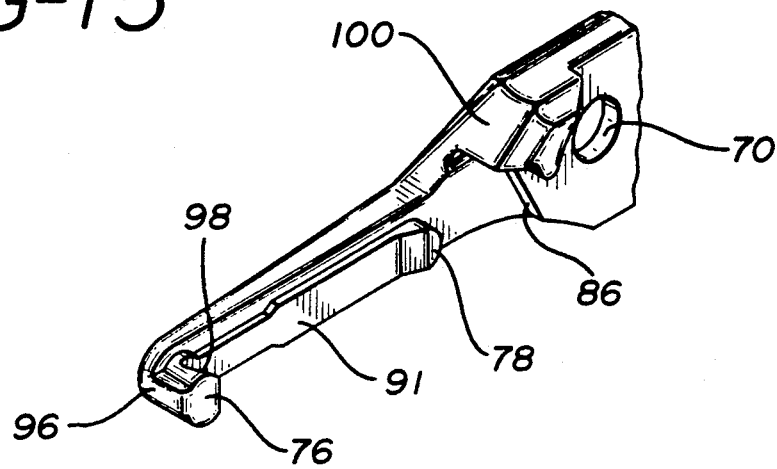

MULTI-DIMENSIONAL SURGICAL BLADE HOLDER AND BLADE COMBINATION

This application is a continuation-in-part of U.S. patent application Ser. No. 612,356, filed Nov. 13, 1990, now U.S. Pat. No. 5,060,387.

BACKGROUND AND DESCRIPTION OF THE INVENTION

The present invention relates to a blade handle or holder which allows for the sequential insertion of a plurality of blades for a single use of each blade with subsequent ejection of the blade from the handle for insertion of an additional blade. More particularly, the invention relates to holders for surgical blades of a precise configuration, and to the blades so configured. Also, this invention involves the handling of contaminated blades in the surgical environment.

As practitioners in the art of surgical blades are aware, AIDS, hepatitis and related contagious diseases present in the blood of patients has made the practice of surgery and medicine, in general, more dangerous than was the case several years ago, simply because one must be extremely careful to avoid contamination of his or her own blood with the blood of an infected patient. For this reason, many devices have been developed for handling instruments to avoid contaminated sharp edges or points which have been contaminated with the blood of infected persons. This is particularly true in the surgical environment where surgical blades are used in great quantity and must be disposed of without being touched, if possible, and certainly without the user being cut or having his or her skin punctured in any way.

Thus, it is important to be able to insert and remove a blade from a holder for the blade, after use, without the user having to actually touch the blade, if possible. If it is necessary to touch the blade, then it is appropriate to touch only the tang portion of the blade and avoid any contact with the sharp edge. It is to this environment that the present invention is directed.

It is equally important in the surgical environment to have the blade held in a holder against any movement relative to the holder. This invention includes blades modified to accommodate a specifically configured holder for this purpose, to the holders, and to the combination of holder and blade. The holder includes opposed cooperating surfaces which capture the blade in three dimensions, so to speak, against any movement in the holder. On the other hand, the blade is configured to meet precisely these opposed cooperating surfaces.

Many arrangements have been developed to obviate the problems discussed above, and to provide blade holders which will hold the blade precisely in the position desired, which will provide ease of insertion so that the user does not cut themselves prior to any use of the blade and/or holder, and that the blade is firmly held against any wobbling or movement in the handle, which would reduce the effectiveness of any surgery being performed with such a blade.

Arrangements have been provided in the past wherein elongated blade holders have been provided of the kind discussed here wherein the two parts of the holder pivot relative to each other for insertion of the blade into the holder and for holding the blade in place. These arrangements have a pivot axis at one end of the two parts forming the holder. With such an arrangement, the user cannot handle removal of the blade single-handedly since it is necessary to use both hands for handling the two pivoting parts. Representative of such arrangements are U.S. Pat. No. 2,245,096 and U.S. Pat. No. 3,906,625. Both of these patents have the pivot axis positioned at the end opposite the end where the blade is inserted.

Other devices of the kind discussed herein include those in which the pivot axis is positioned centrally of the ends of the blade holder. Again, with such arrangements the user must use both hands to manipulate the two parts around the central pivot axis in order to insert and remove the blade. Representative of such prior art patents are U.S. Pat. Nos. 2,478,668 and 2,637,105.

In order to facilitate a single-handed operation for surgical blade holders and the cooperating blade of the kind discussed herein, it is necessary to position the pivot axis adjacent to the position of the blade during use. This enables the user to have a substantially long non-pivoting handle portion to grip for opening and closing the device for insertion and ejection of the blade. Representative of such arrangements are U.S. Pat. Nos. 2,039,443 and 1,914,153. Both of these patents use a separate rotating ejector arrangement which pivots adjacent to the blade for causing the blade to become "unwedged" from its use position for removal of the blade. However, the ejector cams the blade only partially out of its holder arrangement. The user must, after this camming action, grip the blade for final removal from the handle thus risking a cut from the contaminated blade.

With this invention, by contrast, a blade holder is provided for surgical blades which allows the user to open and close the device single-handedly. The arrangement includes a fixed non-rotating half of the handle which has positioned in the blade position thereof, a boss which is configured to be the same as the opening in the tang of the blade to be inserted. As a further feature, this portion of the holder is indented to the same configuration as the blade tang for easy reception of the blade. For this reason, the blade may be positioned on the fixed portion of the handle of the invention.

At one end of the boss is a cooperating abutment which cooperates with the movable portion of the handle in closed position to capture the blade and lock it in a non movable position for use. The other end has a hook or cleat arrangement with an undercut surface which serves to positively position and hold one end of the blade. The opposed half of the blade holder has a distal or nose end that fits under the undercut of the cleat with the blade between. Thus, the user, single handedly, may close the device and wedge the blade in a fixed position effortlessly.

As a further feature of the holder portion of the combination in accordance with this invention, both portions of the holder have wedge features which mate in closed position to hold the ribbed edge of the blade of the invention. The blade portion of the combination herein, includes an opening of expanded width at one end to cooperate with the cleat on the holder. Also, at the very distal end of the expanded width opening is an extension in the hole of the blade which cooperates with a front or distal end of the cleat.

Once the blade has been used, the user may grip the handle, and with the thumb, move the movable portion of the handle open around the pivot axis which is adjacent to the blade. In doing so, the user also places the boss side of the fixed portion of the handle downwardly. For this reason, once the movable portion of the blade handle has been forced open by the thumb of the user, the blade simply falls out of the device into a container used for such purposes in order to contain contaminated sharp instruments. The user does not touch the blade at all once it has been used and contaminated.

As a further feature of the invention here, the blade holder of the invention is substantially flat and the two portions of the handle pivot relative to one another around a pivot with an axis perpendicular to the flat body of the holder, and positioned adjacent to the position of the blade, as discussed above. Moreover, the two portions pivot around this pivot axis in substantially the same longitudinal plane relative to each other. For this reason, the profile of the holder herein is a simplified flat device easily handled and maneuvered in difficult surgical procedures.

Other objects and advantages of this invention will be apparent from the following description, the accompanying drawings and the appended claims.

DESCRIPTION OF THE DRAWINGS

FIG. 1 is a longitudinal side elevational view of the device of the invention in its open position exposing the boss structure for receiving a surgical blade;

FIG. 2 is the structure of FIG. 1 shown in its closed position;

FIG. 5 is a longitudinal end view of the fixed portion or half of the handle of the invention;

FIG. 6 is a side elevational view of the fixed portion of the handle of the invention of FIG. 5 with the rotating portion removed to show the structure of the fixed portion underneath the rotating portion.

FIG. 7 is a longitudinal side elevational view of another embodiment of the device of the invention illustrating the combination blade holder and blade with cooperating interfitting surfaces;

FIG. 8 is a longitudinal edge view of the device of FIG. 7 showing the bottom edge as viewed in FIG. 7;

FIG. 10(*b*) is a side elevational view of blade holder portion of FIG. 10(*a*);

FIG. 12 is a plan view of the blade of the invention;

FIG. 13 is a sectional view along lines 13—13 of FIG. 12;

FIG. 14 is a sectional view along lines 14—14 of FIG. 12; and

FIG. 15 is an isometric view of the blade receiving boss on the long handle portion of the holder of the invention.

DETAILED DESCRIPTION OF THE INVENTION

Figure 3:
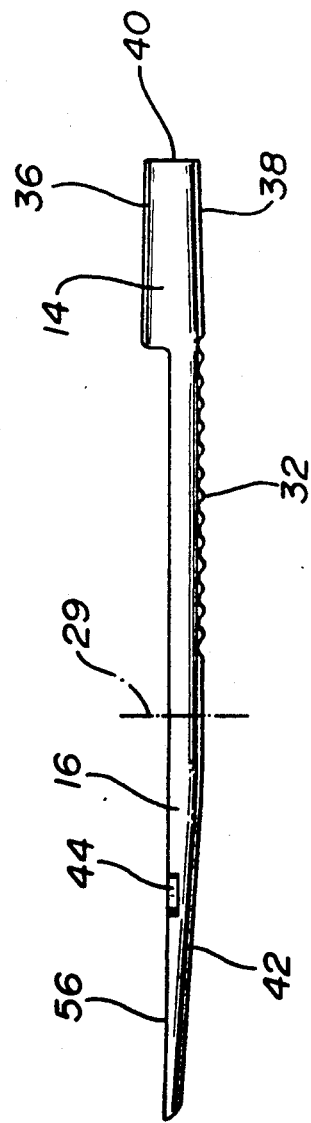
FIG. 3 is a longitudinal end view of the movable handle portion or half of the holder of the invention.

Referring to the drawings in which like reference characters refer to like parts throughout the several views thereof, FIG. 1 shows one embodiment of the surgical blade holder of the invention generally designated 10 in its open position with a fixed handle portion 12 and a rotating handle portion 14. The two halves 12, 14 rotate relative to each other around a pivot axis 29 with a pivot pin 24 for that purpose. In use, however, the smaller half 14 rotates while the portion 12 is held, and therefore, fixed.

The front end portions 16, 18, respectively of the blade holder halves 14, 12, when open, expose a boss 20 having abutments 22, 23 positioned at each end thereof. Boss 20 is configured to be the same as a conventional opening in the tang of a conventional surgical blade for holding the blade in a fixed position once the two portions of the holder 10 are in their closed position as shown in FIG. 2. L-shaped surface 21 (FIG. 6) defines the rear end of the indentation in portion 18 for receiving the blade body.

That is, front end portion 16 of the blade holder movable half moves over the blade itself and the boss 20 to wedge and position both between the two front halves 16, 18 of blade holder 10. When this takes place, of course, the abutments 22, 23 provide a wedging action to hold the blade in a fixed non moving position. In order to provide the appropriate rotating movement around axis 29, the movable and fixed portions 14, 12 of the blade holder of the invention include cooperating opposed curved surfaces 52, 54 and 17, 19. This allows for rotation of the parts relative to each other without any diversion from the desired controlled rotary movement around pivot axis 29 and rotating pin 24.

As can be seen in FIG. 1, movable rotating portion 14 of handle 10 includes a locking extension 26 which is received in a slot 28 in the fixed portion 12 of handle 10. When extension 26 moves into slot 28, there is positioned at the bottom of extension 26 an abutment 48 (FIG. 4), which cooperates with a depression 30, so that 48 snaps in place locking the two parts against relative rotary movement when not desired.

The two halves 12, 14 also include cooperating curved surfaces 42, 40, respectively, again for maintaining a proper relative movement of the two parts around axis 29 and pivot pin 24. The flat surfaces of the movable and fixed parts 12, 14 of the handle include a plurality of spaced vertical ridges 32, 34 which serve to provide the user with a frictional gripping surface during use of the holder, when a blade is fixed in the holder. While cooperating curved surfaces 52, 54 move relative to each other, in the complete open position of FIG. 1, top surface 75 of the movable part 14 moves against the top edge of surface 52 to serve as a stop against further opening movement.

Figure 4:
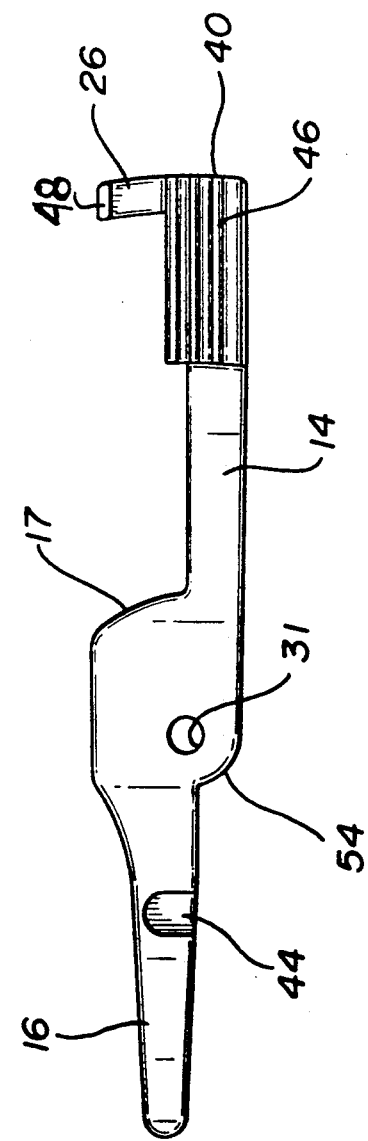
FIG. 4 is a side elevational view of the movable handle portion of the holder of the invention of FIG. 3 showing the opposite side thereof from the showings in FIGS. 1 and 2.

Referring now to FIGS. 3 and 4, these views show the movable portion 14 of the blade holder of the invention separated from the fixed portion thereof for clarity. As can be seen in FIG. 4, this view is the opposite side of portion 14 from that of FIGS. 1 and 2, and 14 includes a plurality of spaced frictional ridges providing a frictional gripping surface 46. This surface serves to provide the user with a frictional surface for the thumb or finger for the opening movement necessary to open the device to allow the blade to drop from the open blade holder 10. Also shown in the surface 56 of the front end portion of the blade half 14 is an opening 44 which cooperates with the abutment 23 on the fixed portion of the device for maintaining the blade fixed between the cooperating surfaces of the fixed and rotating halves of the holder 10 of the invention.

One of the features of the invention, is the fact that the front portion 16 from the pivot axis 29 as shown in FIG. 3 is bowed slightly along the surface 56 to provide a more firm cooperating wedging action between surface 56 and the cooperating surface on the other half 12 of the blade holder 10 of the invention. Both the fixed and rotating halves of the blade holder of the invention include beveled edges 36, 38, which provide a further ease of holding and/or gripping the holder of the invention during use. Finally, referring to FIG. 3, the movable half 14 of the holder of the invention includes a bore 31 for receiving the rotating pivot pin 24.

Referring now to FIGS. 5 and 6, the fixed half 12 of the holder 10 of the invention is shown separately from the movable half thereof. As can be seen in FIGS. 5 and 6, bearing surfaces 52, 53 are shown for cooperating with opposed surfaces on the movable half 14 of the blade 10 of the invention. Surface 53 serves as a "stop" for movement to the closed position of the part 14 in cooperation with the movement of the abutment 48 into the opening 30 to cause locking together of the two halves once the blade is in place between the two halves.

Referring now to FIG. 5, the front end portion 18 is bowed slightly as discussed above relative to surface 56 on rotating or movable part 14 so that the surface 70 cooperates with the opposed surface 56 in a wedging action. This bow is not visible to the human eye since the degree of bow is very small in order to provide appropriate movement of the two parts together, and movement in a non-locking position when required to eject the blade. Fixed blade holder half 12 also includes a bore 27 for receiving the pivot pin 24 as discussed above. The fixed blade holder half 12 includes vertical ridges 34, 35, as viewed in FIG. 6, on opposite sides thereof in order to provide the user with a frictional surface for ease of holding the holder 10 during use.

Thus, in order to use the device 10 of the invention, the user grips the rear end of the fixed portion 12 of the invention. For this purpose, as will be readily seen in FIGS. 1 and 2, a large portion of the elongated device of the invention is removed from any movable part so as to provide a gripping surface for opening and closing the device of the invention. Thereafter, the user places their thumb or finger against the surface 46 for providing a force for opening the movable portion 14 of the invention to expose the boss 20 and opposed locking wedges 22, 23 for receiving the opening of a tang of a blade selected for insertion into the holder 10. This force for opening overcomes the cooperating locking surfaces of the parts 48, 30 of the two halves of the holder of the invention.

Once the holder has been opened, the user may place the blade appropriately with the opening of the blade over the boss 20. Then, the user simply moves the movable holder portion 14 so as to cause the abutment 48 to move in position in the opening 30 for locking the two parts together. With this movement, the blade is fixed in place with no "wobbling" in the holder. Then the user may use the holder with the blade in an appropriate desired way.

Subsequent to use, the contaminated blade may be removed readily by the user. This is done simply by, again, holding the rear end of the fixed portion of the device of the invention and placing the thumb or finger against the frictional surface 46 for movement of the rotating portion 14 around pivot axis 29. This force overcomes the locking engagement of cooperating parts 30, 48 and allows the two parts to open to a position as shown in FIG. 1. Thereafter, the user may, if the boss 20 is positioned upwardly, simply turn the holder so that the boss is positioned downwardly and the blade will fall out into a container provided for that purpose.

For this reason, the user's hands are not contaminated by any blood on a blade which has been used in the holder of the invention. There is no required movement on the part of the user of any kind to touch or remove the blade from the holder. It simply falls from the holder when the holder is opened, as discussed above.

FIGS. 7 and 8 show a further embodiment of a surgical blade holder 60. However, in this embodiment, a combination blade and holder are provided in which both the blade and the holder have specifically configured cooperating surfaces to hold the blade fixed in the holder in an appropriate fashion. The holder is so configured that only blades with an opening configured in accordance with this invention will hold the blade. The embodiment shown in FIGS. 7 and 8 has a rotating and a fixed half 64, 62, respectively, in the same manner as the embodiment shown and described in FIGS. 1–6. The two halves rotate around a pivot axis 70 in the same manner. Moreover, the smaller rotating half has a locking tab 61 in the same manner as the embodiment shown and described in FIG. 1.

The difference lies in the specific blade opening boss configuration including a cleat 76 and abutment 78 spaced apart to cooperate with a specific opening configuration in the blade 66 of the invention. As shown in FIG. 8, the spaced apart abutment 78 and cleat 76 are positioned on the fixed longer portion 62 of the holder 60 of the embodiment of FIGS. 7 and 8. Further as shown in FIG. 7, the fixed portion 62 of the holder 60 includes measurements 68 which are utilized by the surgeon during surgery for measuring the dimension of an incision made by blade 66. As shown in FIG. 8, further, this embodiment 60 of the invention also includes beveled edges 80, 82 and the cooperating textured surfaces 72, 74 to assist in holding the holder 60 of the invention in a precise manner during surgical procedures.

Figure 9:
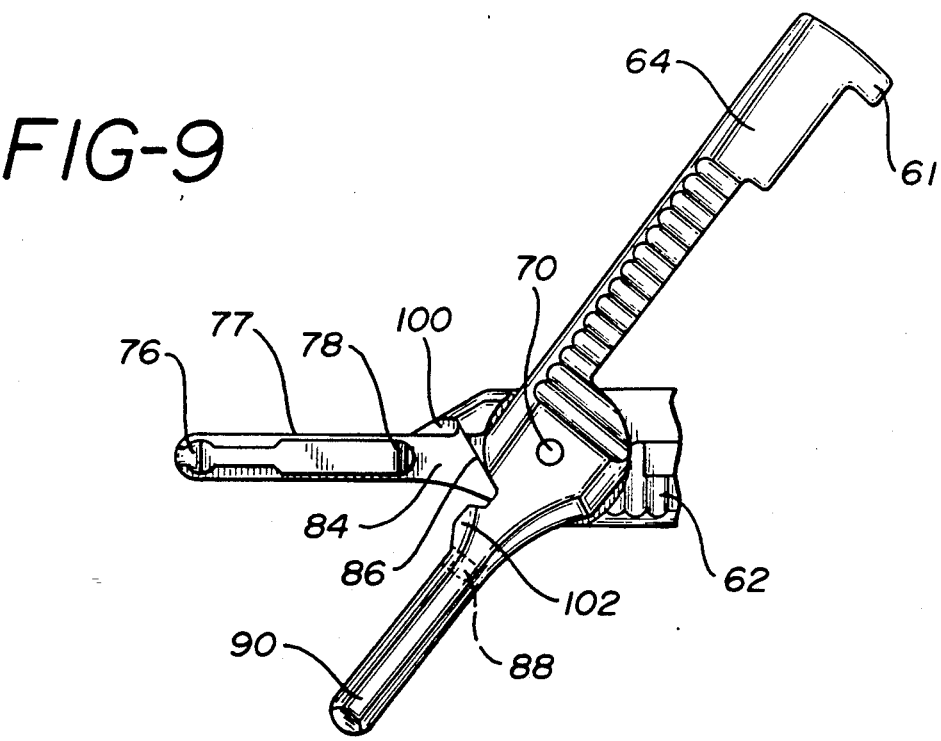
FIG. 9 is a partial longitudinal view of the device of FIG. 7 shown in open position, and showing the cooperating surfaces for the blade with the blade removed.

Referring now to FIG. 9, the specific boss configuration of the fixed portion 62 of holder 60 is shown with the spaced apart cleat 76 and abutment 78. As can be seen in FIG. 9, a specific mating feature 100 on the fixed portion of the holder 60 and 102 on the movable portion 64 cooperate with each other to grip the rib back 114 of the blade 66 (FIG. 13). Because of this, the rib 114 of blade 66 is securely captured in both halves of the handle and serves to increase the secure three dimensional stability of the blade in the holder of the invention.

As can be seen in FIG. 9, further, distal end 90 of the movable portion 64 of the invention includes an opening 88 for receiving therein the abutment 78 on surface 84 in the closed position of holder 60.

Figure 10A:
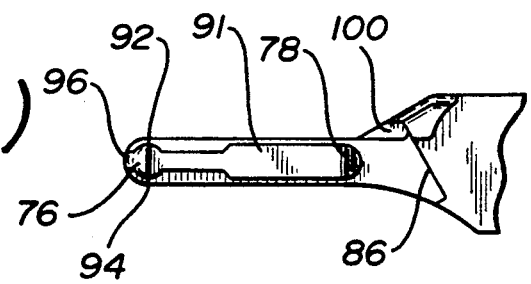
FIG. 10(*a*) is a partial longitudinal view of the long fixed handle portion of the blade holder showing the blade mating surface details.
Figure 10B:
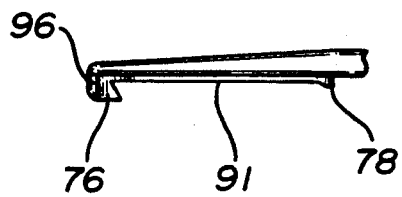
Figure 11:
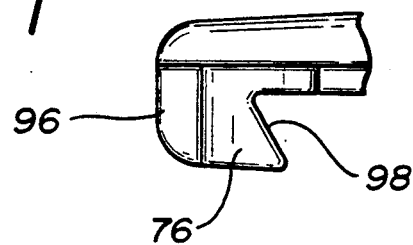
FIG. 11 is an enlarged partial view of FIG. 10(*b*) showing details of the cleat on the holder of the invention for cooperating with the opening in the blade of the invention.

Referring now to FIGS. 10(a) and 10(b), boss 91 includes the distal cleat 76 which has a forward extension 96. Cleat 76 extends on each side to points 92, 94 for cooperating with the mating surfaces of blade 66, as will be described in more detail below. As can be seen in FIG. 11, in the enlarged view of cleat 76, the cleat has an overhang surface 98 which serves to lock the blade in place and for cooperating with the distal end of the opening of blade 66 which opening is specifically configured to cooperate only with the holder 60 described herein.

Prior to describing the configuration of the blade of the invention, reference is made to FIG. 15 which shows an isometric or perspective view of distal end 77 of the fixed portion 62 of blade 60. As can be seen in FIG. 15, boss 91 is configured for receiving a specific blade opening and shows the spaced apart abutment 78, cleat 76, as well as the rear mating surface 86 for receiving the proximal end of blade 66. Also, the view in FIG. 15 shows the surface 100 for cooperating with surface 102 for engaging the ribbed portion 114 of blade 66.

Referring now to FIGS. 12, 13 and 14, blade 66 of the invention is shown. As can be seen in FIG. 12, blade 66 has a specifically configured opening 65 with the proximal end of opening 65 being 108 for engaging abutment 78. However, as shown in FIG. 12, the distal end 104, 106 of opening 65 is configured substantially differently from conventional blade openings for surgical blades. That is, the distal end includes an enlarged round shaped opening 104 for receiving and engaging cleat 76 with the distal extension 106 for receiving the extension 96 of cleat 76. Because of the undercut or overhang surface 98 of cleat 76, the blade is held in a more substantial position between the two halves of the holder 60 when the holder is in its closed position.

FIG. 13 shows a sectional view of the ribbed area 114 on the top surface of blade 66. FIG. 14 shows the opposed tapers 116, 118 of blade 66 forming the cutting edge 112 of blade 66.

Thus, as will be appreciated from the above, there is provided in accordance with this invention two forms of surgical blade holders which are relatively simple and uncomplicated in construction and easily stamped from a selected material such as stainless steel in a mass production line. In both arrangements, the user may insert a blade in a very simple manner and, again remove the blade without ever touching the blade if it should be in fact contaminated. It should be understood, of course, that one embodiment of holder of the invention may be used for blades other than surgical blades, or with conventional surgical blades. The simplicity of the structure is such that many uses may be provided with the holder of the type described. However, it is also important to note that the holder of the invention, regardless of its simplicity, holds the blade in a complete fixed position with no movement in the holder. This allows the user to provide a precise cutting action as desired for the use of the blade being selected.

While the holder configured to fit the specific blade of the invention here is also easily stamped from stainless steel, for example, and may be easily loaded and unloaded with the blade of the invention, it has surfaces specifically configured on each half thereof to mate with the specific blade configuration of the invention.

Again, while the blade of the invention is simple to use and to manufacture, it has been developed with precisely arranged surfaces for three dimensional mating with the holder in accordance herewith. Because of this the blade is fixed from movement in any dimensional direction of its position in the cooperating holder.

While the forms of apparatus herein described constitute preferred embodiments of the invention, it is to be understood that the invention is not limited to these precise forms of apparatus, and that changes may be made therein without departing from the scope of the invention which is defined in the appended claims. As discussed above, the device of the invention is comprised of two very simple parts which may be readily stamped from a selected material in a mass production line.

What is claimed is:

1. A blade holder, comprising
   (a) an elongated flat fixed body portion;
   (b) a blade receiving area at a first end of said elongated fixed body portion for receiving the tang of a blade;
   (c) said blade receiving area being an elongated integral boss;
   (d) said elongated integral boss having a cleat positioned proximal the said first end of said fixed body portion and an abutment positioned distal the said first end of said fixed body portion;
   (e) a handle gripping area at a second end of said fixed body portion opposite said blade receiving area;
   (f) a pivot pin on said flat fixed body portion intermediate said fist and second ends and adjacent said blade receiving area;
   (g) the axis of said pivot pin being perpendicular to said flat fixed body portion;
   (h) an elongated flat rotatable body portion;
   (e) said rotatable body portion rotatable around said pivot pin from an open position for receiving a blade in said blade receiving area to a closed position wherein the cooperating opposed surfaces of said fixed body portion and said rotatable body portion lock a blade tang in said blade receiving area; and
   (j) cooperating locking means on said flat fixed body portion and said rotatable body portion for locking the tang of a blade in aid blade receiving area.

2. The blade holder of claim 1, wherein
   (a) said boss is configured to be the same shape as the opening in the tang of a blade to be received thereover.

3. The blade holder of claim 1, wherein said cleat includes an undercut extending toward said abutment for engaging and overhanging said cooperating opposed surface of said rotatable body portion wherein said cleat undercut and said opposed surface engage the end of an opening in a blade positioned in said holder.

4. The blade holder of claim 1, wherein said cooperating locking means includes
   (a) a curved slot on said elongated fixed body portion;
   (b) an indentation at the end of said curved slot;
   (c) a curved extension on said rotatable body portion at the end thereof opposite said blade receiving area; and
   (d) a locking abutment on the end of said curved extension for extending into said indentation at the end of said curved slot.

5. The blade holder of claim 1, further comprising
   (a) frictional gripping surfaces on each side of said fixed and rotatable body portions for holding said blade holder during use.

6. The blade holder of claim 4, further comprising
   (a) a frictional gripping surface on the side of said flat rotatable body portion opposite said curved locking extension for urging said flat rotatable body portion to the open position;
   (b) said frictional gripping surface having ribs oriented parallel to the longitudinal extent of said rotating body portion.

7. The blade holder of claim 1, further comprising a surgical blade said blade comprising
   (a) a flat elongated body with opposed side edges;
   (b) said elongated body extending from a first blade end to a second blade end;
   (c) a blade cutting edge extending along one of said opposed side edges from a point intermediate said first and second blade ends to said first end;
   (d) said second blade end having an angled surface for engaging an opposed surface on said holder;
   (e) a handle boss receiving opening in said blade;
   (f) said opening extending from a point spaced from said first blade end to a point spaced from said second blade end;
   (g) said opening having a wide portion at the end thereof adjacent said second blade end and a narrow portion at the end thereof spaced from said first blade end; and
   (h) said narrow portion having a round widened cleat engaging portion at the end thereof immediately adjacent said first blade end.

8. The holder of claim 7, wherein said blade further comprising
   (a) a rib extending along the said side edge opposite to said side edge having said blade cutting edge.

9. A combination surgical blade holder and interfitting surgical blade, comprising
   (a) a blade holder body;
   (b) said blade holder body having an elongated fixed portion and a shorter rotatable portion;
   (c) a blade receiving area at a first end of said elongated fixed body portion for receiving the tang of a blade and a handle portion at the a second end of said elongated fixed body portion opposite sad first end;
   (d) a pivot point intermediate said first and second ends of said elongated fixed body portion on said blade holder adjacent said blade receiving area for pivoting said shorter rotatable portion of said holder on said elongated fixed portion;
   (e) a surgical blade;
   (f) an integral blade receiving boss on said blade receiving area;
   (g) a boss receiving opening in said surgical blade;
   (h) said boss and said boss receiving opening being elongated and configured the same to have equal cooperating opposed surfaces; and
   (i) said boss and said boss receiving opening including
      (1) a wide portion at the end adjacent said pivot point;
      (2) a narrow portion extending toward said first end;
      (3) said narrow portion having a round widened area immediately adjacent said first end; and
      (4) said round widened area having a narrow square portion extending toward said first end;
   (j) whereby said rotatable portion of said blade holder body rotates around said pivot point from an open position for positioning said boss receiving opening on said blade receiving boss to a closed position locking said blade in said blade receiving area.

10. The combination of claim 9, further comprising:
   (a) a cleat positioned proximal said first end of said fixed body portion;
   (b) an abutment positioned distal said first end of said fixed body portion; and
   (c) said round widened area and said narrow square portion of said blade boss receiving opening for receiving said cleat.

11. The combination of claim 10, wherein
   (a) said cleat having an undercut surface extending proximally of said boss;
   (b) said undercut surface for engaging the end of said rotatable portion of said blade holder adjacent said first end; and
   (c) said cleat undercut surface and said end of said rotatable blade holder portion adjacent said first end for receiving the end adjacent said first end of said boss receiving opening in said blade.

12. A blade holder, comprising
   (a) an elongated flat fixed body portion;
   (b) a blade receiving area at a first end of said elongated fixed body portion for receiving the tang of a blade;
   (c) said blade receiving area including at least one integral boss for facilitating receipt of said blade;
   (d) said blade receiving area having a cleat positioned proximal the said first end of said fixed body portion and an abutment positioned distal the said first end of said fixed body portion;
   (e) a handle gripping area at a second end of said fixed body portion opposite said blade receiving area;
   (f) a pivot pin on said flat fixed body portion intermediate said first and second ends and adjacent said blade receiving area;
   (g) the axis of said pivot pin being perpendicular to said flat fixed body portion;
   (h) an elongated flat rotatable body portion;
   (i) said rotatable body portion rotatable around said pivot pin from an open position for receiving a blade in said blade receiving area to a closed position wherein the cooperating opposed surfaces of said fixed body portion and said rotatable body portion lock a blade tang in said blade receiving area; and
   (j) cooperating locking means on said flat fixed body portion and said rotatable body portion for locking the tang of a blade in said blade receiving area.

* * * * *